(12) United States Patent
Kamochi et al.

(10) Patent No.: US 6,706,665 B2
(45) Date of Patent: Mar. 16, 2004

(54) METHOD FOR INCREASING THE YIELD OF BEANS

(75) Inventors: Atsumi Kamochi, Oyama (JP); Michiaki Shiroshita, Koga (JP)

(73) Assignee: Nihon Bayer Agrochem K. K., Tokyo (JP)

( * ) Notice: Subject to any disclaimer, the term of this patent is extended or adjusted under 35 U.S.C. 154(b) by 0 days.

(21) Appl. No.: 10/220,721

(22) PCT Filed: Mar. 5, 2001

(86) PCT No.: PCT/IB01/00306
§ 371 (c)(1), (2), (4) Date: Sep. 4, 2002

(87) PCT Pub. No.: WO01/65943
PCT Pub. Date: Sep. 13, 2001

(65) Prior Publication Data
US 2003/0040438 A1 Feb. 27, 2003

(30) Foreign Application Priority Data
Mar. 7, 2000 (JP) .......................................... 2000-61753

(51) Int. Cl.$^7$ .......................... A01N 37/26; A01N 53/00
(52) U.S. Cl. ...................................................... 504/334
(58) Field of Search ........................................ 504/334

(56) References Cited

U.S. PATENT DOCUMENTS 4,556,409 A   12/1985   Fayter, Jr. et al. ............... 71/76

2001/0007874 A1 * 7/2001 Oostendorp et al. ........ 514/361

FOREIGN PATENT DOCUMENTS

EP    0 341 475    11/1989

OTHER PUBLICATIONS

"Noyaku Yoran" (Agrochemicals Handbook) (month unavailable) 1999, p. 546–547, published by Nippon Shokubutsu Boeki Kyokai (Japan Plant Protection Association) (Translation attached also).

* cited by examiner

*Primary Examiner*—S. Mark Clardy
(74) *Attorney, Agent, or Firm*—Richard E. L. Henderson

(57) ABSTRACT

The invention relates to N-(R)-[1-(4-chloro-phenyl)-ethyl]-2,2-dichloro-1-ethyl-3t-methyl-1r-cyclopropanecarboxamide of the formula

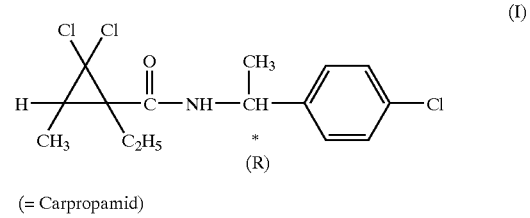

(= Carpropamid)

which is very suitable for increasing the yield of beans.

8 Claims, No Drawings

METHOD FOR INCREASING THE YIELD OF BEANS

The present invention relates to a new method for increasing the yield of beans by means of a known cyclopropanecarboxamide.

It has already been known that the yield of crops can be increased by breeding plant varieties providing high yields of the harvested products, or by methods for chemically regulating the plant growth etc. Moreover, there have recently been conducted methods for artificially producing plant varieties with high yields by using plant gene recombinant technology.

As to beans, as a positive method for increasing the yield, particularly plant breeding has been adopted hitherto, whereas a method for chemical regulation of the plant growth has not been conducted until now.

It has also been described already that N-(R)-[1-(4-chloro-phenyl)-ethyl]-2,2-dichloro-1-ethyl-3t-methyl-1r-cyclopropanecarboxamide (=Carpropamid) shows fungicidal activity and can particularly be employed for the control of *Pyricularia oryzae* on rice (see EP-A 0 341 475).

It has now been found that N-(R)-[1-(4-chloro-phenyl)-ethyl]-2,2-dichloro-1-ethyl-3t-methyl-1r-cyclopropanecarboxamide of the formula

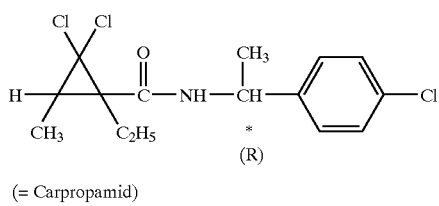

(= Carpropamid)

is very suitable for increasing the yield of beans.

Thus, the present invention consists in a method for increasing the yield of beans by treating the plants and/or their habitat, particularly the seeds and/or their habitat, with the compound of the formula (I).

It is very surprising that the compound of the formula (I) according to the invention is outstandingly effective for increasing the yield of beans, since it has only been known until now that this compound is suitable for the control of fungi.

The structural formula (I) shows that the compound comprises three asymmetrically substituted carbon atoms, wherein the carbon atom between the NH-group and the phenyl ring has the R-configuration. Thus, the product can be present as a mixture of isomers or in the form of a single optically active component. The individual isomers are the N-(R)-[1-(4-chloro-phenyl)-ethyl]-(1S)-2,2-dichloro-1-ethyl-3t-methyl-1r-cyclopropanecarboxamide of the formula

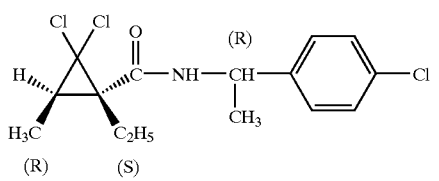

and the N-(R)-[1-(4-chloro-phenyl)-ethyl]-(1R)-2,2-dichloro-1-ethyl-3t-methyl-1r-cyclopropanecarboxamide of the formula

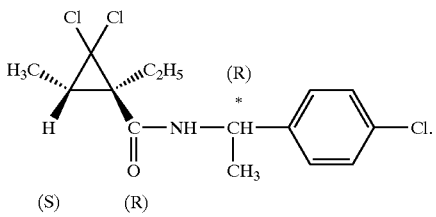

The compound of the formula (I) and the individual isomers thereof are known (see EP-A 0 341 475).

The compound of the formula (I) according to the invention has the common name "Carpropamid". It is well known as a fungicide for agricultural use (cf. "NOYAKU YORAN" (Agrochemicals Handbook) 1999, p. 546–547, published by NIPPON SHOKUBUTSU BOEKI KYOKAI (Japan Plant Protection Association). Hereinafter the compound of the formula (I) is referred to as "Carpropamid".

Carpropamid is very effective for increasing the yield of beans. For this purpose, it is preferably applied to the seeds of beans before sowing.

When the yield increasing agent according to the invention is practically used, seeds of beans can be previously treated, specifically, for example, they can be drenched or dressed with formulations comprising Carpropamid, preferably before sowing.

In case of drenching, for example, seeds of beans are drenched for a period of time between 10 minutes and 16 hours by usually using a liquid formulation comprising Capropamid, preferably comprising the active compound at a concentration between 1 ppm and 1000 ppm, particularly preferably between 2.5 ppm and 500 ppm. By sowing and cultivating these treated seeds of beans, an increase in yield of beans can be achieved.

In case of seed dressing, seeds of beans are in general dressed by using powders, wettable powders etc. comprising in general between 0.05 and 30% by weight, particularly between 0.1 and 25% by weight of Carpropamid. By sowing and cultivating seeds of beans thus treated, the yield of beans can be increased.

Further, it is possible to treat the seeds of beans themselves with coating agents comprising Capropamid.

Furthermore, when the yield increasing agent according to the present invention is used, it is also possible to treat the seeds of beans with Carpropamid by soil-treatment, for example by mixing Carpropamid with the soil or by spreading, in each case before sowing the seeds.

As specific examples of beans, whose yield can be increased by using the yield increasing agent of the present invention, there can be mentioned, for example, soybeans, peas, adzuki beans, peanuts, kidney beans etc.

In order to use Carpropamid as a yield increasing agent, it can be applied in the form of various types of formulations. In case of using Carpropamid by drenching, the formulations can be used in the form of liquid formulations, and as specific examples thereof there may be mentioned wettable powders, water-dispersible granules, solutions, liquids, AL formulations, aqueous suspensions etc. and in case of seed dressing there may be mentioned powders, wettable powders etc. Further, seed coating agents can may be mentioned.

In case of mixing Carpropamid with the soil, powders are mentioned as a preferred examples.

These formulations can be prepared by per se known methods, for example, by mixing Carpropamid with extenders, namely liquid or solid diluents or carriers, optionally together with surface-active agents, namely emulsifiers and/or dispersants. In case of using water as an extender, an organic solvent for example, can be used as an auxiliary solvent.

As liquid diluents or carriers there can be generally mentioned aromatic hydrocarbons (for example, xylene, toluene, alkylnaphthalene etc.), chlorinated aromatic or chlorinated aliphatic hydrocarbons (for example, chlorobenzenes, ethylene chlorides, methylene chloride etc.), aliphatic hydrocarbons [for example, cyclohexane etc. or paraffins (for example, mineral oil fractions etc.)], alcohols (for example, butanol, glycol and their ethers, esters etc.), ketones (for example, acetone, methyl ethyl ketone, methyl isobutyl ketone, cyclohexanone etc.), strongly polar solvents (for example, dimethylformamide, dimethyl sulphoxide etc.), water etc.

As solid diluents there can be mentioned, for example, ground natural minerals (for example, kaolin, clay, talc, chalk, quartz, attapulgite, montmorillonite, diatomaceous earth etc.), ground synthetic minerals (for example, highly dispersed silicic acid, alumina, silicates etc.) etc.

As solid carriers for granules there can be mentioned, for example, crushed and fractionated rocks (for example, calcite, marble, pumice, sepiolite, dolomite etc.), synthetic granules of inorganic and organic meals, particles of organic materials (for example, sawdust, coconut shells, maize cobs, tobacco stalks etc.).

As surface-active agents there can be mentioned nonionic and anionic surface-active agents, for example, polyoxyethylene fatty acid esters, polyoxyethylene fatty acid alcohol ethers (for example, alkylaryl polyglycol ethers), alkylsulphonates, alkylsulphates, arylsulphonates etc.

Dispersants include, for example, ligninsulphite waste liquor and methyl cellulose.

Tackifiers can also be used in formulations (powders, granules, emulsions). As said tackifiers there can be mentioned, for example, carboxymethyl cellulose, natural and synthetic polymers (for example, gum arabic, polyvinyl alcohol, polyvinyl acetate etc.).

Colorants can also be used. As said colorants there can be mentioned inorganic pigments (for example, iron oxide, titanium oxide, Prussian Blue etc.), organic dyestuffs (for example, alizarin dyestuffs, azo dyestuffs, metal phthalocyanine dyestuffs etc.), and trace nutrients such as salts of iron, manganese, boron, copper, cobalt, molybdenum, zinc etc.

Said formulations can contain generally between 0.1 and 95% by weight, preferably between 0.5 and 90% by weight of Carpropamid.

In case of seed treatment, Carpropamid can be used in the proportion of generally between 0.001 and 1 g, preferably between 0.01 and 0.2 g per 1 kg of seeds.

Further, in case of soil treatment, Carpropamid can be used at the concentration of 0.00001–0.5% by weight, preferably 0.0001–0.1% by weight at the point of action.

Then the present invention will be described more specifically by examples. However, the present invention should not be restricted to them in any way. Parts in compounding amounts mean parts by weight.

EXAMPLES

Test Example 1
Test of Yield Increasing Effect on Soybeans
Preparation of a Solution
1 Part by weight of Carpropamid, 20 parts by weight of N,N-dimethylfonnamide and 3 parts by weight of surface-active agent (methanol:Sorpol BDB:Sorpol DS=2:1:1) were mixed and diluted with distilled water to the prescribed concentration.

Testing Procedure
30 Grains of soybean seeds (Variety: Halosoy) were drenched in the solution of the prescribed concentration prepared as mentioned above for 12 hours and these drenched bean seeds were sown in the proportion of 2 grains per point with 20 cm distance between the stocks and at 2 cm depth. After germination they were thinned out so that one better grown plant remained at each point. They were controlled as soybean cultivation until harvest after 110 days after sowing.

Soybean plants were pulled out at the harvest time, dried by hanging in a cold and dark place. After that the grains were threshed and dried in a drier (100° C., 8 hours) so that the water content in soybeans became uniform.

Before pulling out, the number of the abortive pods and the number of the grown pods were counted. After threshing, dried plants were weighed. After soybeans had been dried, the number of grains, one grain weight and total grain weight for each treated section were measured. In the non-treated section, soybeans were drenched in tap water for 10 minutes, sown without drying in the air, and cultivated in the same manner.

Yield increasing index (%): Yield increasing index when yield (g) in the non-treated section is 100%.

Productive grain increasing index (%): Increasing index when average number of the productive grains in the non-treated section is 100% (calculated based upon the number of the productive grains per plant after selection of soybeans).

One grain weight (g): Weight per grain of a selected bean, after eliminating unripe beans and beans out of standard by selection, after threshing and drying the soybeans (no significant difference by F statistical test)

Results
Test results are shown in Table 1.

TABLE 1

| Active component | Concentration (ppm) | Yield increasing index per plant (%) | Productive grain increasing index (%) | One grain weight (g) |
| --- | --- | --- | --- | --- |
| Carpropamid | 1000 | 132.2 | 126.8 | 0.23 |
| Carpropamid | 100 | 169.1 | 163.4 | 0.23 |
| Carpropamid | 10 | 173.1 | 163.5 | 0.23 |
| Carpropamid | 1 | 131.1 | 127.1 | 0.23 |
| non-treated | — | 100 | 100 | 0.22 |

FORMULATION EXAMPLES

FORMULATION EXAMPLE 1

Water-dispersible Granules

20 Parts of Carpropamid, 30 parts of sodium ligninsulfonate, 15 parts of bentonite and 35 parts of calcined diatomaceous earth powder were thoroughly mixed with water. The resulting product was granulated by means of extrusion through a 0.3 mm screen. After drying the product, water-dispersible granules were obtained.

FORMULATION EXAMPLE 2

Aqueous Suspension

4 Parts of Carpropamid, 3 parts of Newkalgen FS-26 (made by Takemoto Oil & Fat Co., Ltd.; a compounded surface-active agent of polyoxyethylene tristyryl phenyl ether and sodium dioctyl sulfosuccinate), 0.5 parts of SAG-10 (made by Nippon Unicar Co., Ltd.; 14% silicone emulsion), 10 parts of glycerol, 0.18 parts of xanthan gum, 1 part of bentonite, 0.06 parts of potassium dihydrogen phosphate and 81.26 parts of water were stirred and ground in a Dyno mill to make a uniform aqueous suspension.

What is claimed is:

1. A method for increasing the yield of beans comprising applying
carpropamid as the only yield-increasing compound to beans and/or to the habitat of beans.

2. A method according to claim 1 wherein carpropamid is applied to seeds of the beans before sowing.

3. A method according to claim 1 wherein carpropamid is applied to seeds of the beans by drenching.

4. A method according to claim 1 wherein carpropamid is applied to seeds of the beans by dressing.

5. A method according to claim 1 wherein carpropamid is applied to seeds of the beans by treating the soil with the compound of the formula (I) before sowing the seeds.

6. A method according to claim 3 wherein the seeds are drenched with a liquid formulation comprising carpropamid in a concentration between 1 and 1000 ppm.

7. A method according to claim 3 wherein the seeds are drenched for a period of time between 10 minutes and 16 hours.

8. A method according to claim 1 wherein carpropamid is applied as the only yield-increasing compound to seeds of soybeans, peas, adzuki beans, or kidney beans.

* * * * *